United States Patent
Anzai (10) Patent No.: US 10,751,521 B2
(45) Date of Patent: Aug. 25, 2020

(54) MEDICAL INSTRUMENT

(71) Applicant: TERUMO KABUSHIKI KAISHA, Tokyo (JP)

(72) Inventor: Takao Anzai, Kanagawa (JP)

(73) Assignee: TERUMO KABUSHIKI KAISHA, Shibuya-Ku, Tokyo (JP)

( * ) Notice: Subject to any disclaimer, the term of this patent is extended or adjusted under 35 U.S.C. 154(b) by 34 days.

(21) Appl. No.: 16/118,804

(22) Filed: Aug. 31, 2018

(65) Prior Publication Data
US 2018/0369556 A1 Dec. 27, 2018

Related U.S. Application Data (63) Continuation of application No. PCT/JP2017/005982, filed on Feb. 17, 2017.

(30) Foreign Application Priority Data

Mar. 8, 2016 (JP) .................................. 2016-044663

(51) Int. Cl.
*A61M 39/08* (2006.01)
*A61M 25/00* (2006.01)
(Continued)

(52) U.S. Cl.
CPC ............ *A61M 39/08* (2013.01); *A61M 25/00* (2013.01); *A61M 39/12* (2013.01); *F16L 31/00* (2013.01);
(Continued)

(58) Field of Classification Search
CPC ...... A61M 39/08; A61M 25/00; A61M 39/12; A61M 1/3666; A61M 2039/087; A61M 2207/00; F16L 31/00; F16L 2201/44
(Continued)

(56) References Cited

U.S. PATENT DOCUMENTS 3,850,202 A * 11/1974 Morgan ................. A61M 39/04
138/103
4,052,990 A * 10/1977 Dodgson ............ A61M 16/0816
128/207.14
(Continued)

FOREIGN PATENT DOCUMENTS

JP S61213057 A 9/1986
JP H04152952 A 5/1992
(Continued)

OTHER PUBLICATIONS

The extended European Search Report dated Oct. 25, 2019, by the European Patent Office in corresponding European Patent Application No. 17762870.8-1132. (6 pages).
(Continued)

*Primary Examiner* — Craig M Schneider
*Assistant Examiner* — David R Deal
(74) *Attorney, Agent, or Firm* — Buchanan Ingersoll & Rooney PC (57) ABSTRACT

A medical instrument includes a first tube body and a second tube body joined to the first tube body by being inserted in the lumen of the first tube body. The second tube body is more rigid than the first tube body. The medical instrument includes a coating layer made of a biocompatible material disposed on the inner peripheral surfaces of the first and second tube bodies. The inner peripheral surface of the second tube body is radially inward of the inner peripheral surface of the first tube body to create a level difference portion. The thickness of the part of the coating layer which coats the level difference portion is larger than the thickness of the level difference portion.

20 Claims, 6 Drawing Sheets

(51) Int. Cl.
*A61M 39/12* (2006.01)
*F16L 31/00* (2006.01)
*A61M 1/36* (2006.01)

(52) U.S. Cl.
CPC ..... *A61M 1/3666* (2013.01); *A61M 2039/087* (2013.01); *A61M 2205/0238* (2013.01); *A61M 2207/00* (2013.01); *F16L 2201/44* (2013.01)

(58) Field of Classification Search
USPC .................................................. 138/137, 140
See application file for complete search history.

(56) References Cited

U.S. PATENT DOCUMENTS

| | | | |
|---|---|---|---|
| 4,064,619 A | | 12/1977 | Echols et al. |
| 4,551,292 A | * | 11/1985 | Fletcher ............... A61M 25/001 264/139 |
| 4,636,346 A | * | 1/1987 | Gold .................... A61M 25/001 138/109 |
| 4,806,182 A | | 2/1989 | Rydell et al. |
| 5,254,249 A | | 10/1993 | Terada et al. |
| 5,533,985 A | * | 7/1996 | Wang ................ A61M 25/0009 604/264 |
| 6,217,566 B1 | * | 4/2001 | Ju ....................... A61M 25/005 604/526 |
| 7,892,215 B2 | * | 2/2011 | Melsheimer ............. A61F 2/95 604/103.04 |
| 2010/0198192 A1 | * | 8/2010 | Serina ................ A61B 1/00078 604/523 |
| 2013/0310767 A1 | * | 11/2013 | Solar ................. A61M 25/0068 604/247 |
| 2014/0200550 A1 | * | 7/2014 | Farnan ................ A61M 1/3653 604/509 |

FOREIGN PATENT DOCUMENTS

| | | |
|---|---|---|
| JP | 2001000533 A | 1/2001 |
| WO | 9012607 A1 | 11/1990 |
| WO | 2014123077 A1 | 8/2014 |

OTHER PUBLICATIONS

An English Translation of the International Search Report (Form PCT/ISA/210) and the Written Opinion of the International Searching Authority (Form PCT/ISA/237) dated Jun. 13, 2017, by the Japanese Patent Office in corresponding International Application No. PCT/JP2017/005982. (10 pages).

International Search Report (PCT/ISA/210) dated Jun. 13, 2017, by the Japanese Patent Office as the International Searching Authority for International Application No. PCT/JP2017/005982.

Written Opinion (PCT/ISA/237) dated Jun. 13, 2017, by the Japanese Patent Office as the International Searching Authority for International Application No. PCT/JP2017/005982.

* cited by examiner

MEDICAL INSTRUMENT

CROSS-REFERENCES TO RELATED APPLICATIONS

This application is a continuation of International Application No. PCT/JP2017/005982 filed on Feb. 17, 2017, which claims priority to Japanese Patent Application No. 2016-044663 filed on Mar. 8, 2016, the entire content of both of which is incorporated herein by reference.

TECHNICAL FIELD

The present invention generally relates to a medical instrument and a method for manufacturing a medical instrument.

BACKGROUND DISCUSSION

In the medical field, a medical instrument may be used as a blood circuit constituting an extracorporeal circulation circuit or the like in some cases. The medical instrument includes a tube body (hereinafter, referred to as a first tube body) which is flexible and a tube body (hereinafter, referred to as a second tube body) such as a connector, which has a rigidity higher than that of the first tube body (i.e., the second tube body is more rigid than the first tube body) and is fitted in the first tube body. When the medical instrument is used, blood circulates through a lumen of the first tube body and a lumen of the second tube body. Therefore, an inner peripheral surface of each tube body is provided with a coating layer having biocompatibility (i.e., a biocompatible coating is applied to the inner surface of the first and second tube bodies).

The coating layer is made of various types of materials which are available. For example, Japanese Patent Application Publication No. H04-152952 discloses a medical instrument that uses a synthetic polymer having biocompatibility and antithrombotic.

SUMMARY

The part of a general medical instrument with which blood or body fluids come into contact is provided with a coating layer, and thereby a function of the coating layer is considered to be sufficiently maintained. However, in a medical instrument in which a second tube body is inserted into a first tube body such that both tube bodies are joined to each other, a level difference portion is formed between an inner peripheral surface of the first tube body and an inner peripheral surface of the second tube body, depending on a thickness of a tube wall of the second tube body. In addition, when the first tube body and the second tube body have different rigidity from each other, and the medical instrument is curved or the like in a state in which both tube bodies are joined to each other, stress is concentrated on the periphery of the level difference portion. The coating layer can thus be broken at this location with the periphery of the level difference portion as a starting point.

The disclosed medical instrument includes a first tube body and a second tube body which have different rigidity from each other, in which it is possible to prevent a coating layer in a level difference portion (which is formed between the tube bodies) from being broken.

The disclosed medical instrument includes: a first tube body that has a lumen; a second tube body that has a lumen and has rigidity higher than that of the first tube body; and a coating layer made of a biocompatible material, which is disposed on an inner peripheral surface of the first tube body and an inner peripheral surface of the second tube body. The first tube body is joined to the second tube body in a state in which a distal end opening portion of the second tube body is inserted into the lumen of the first tube body. A level difference portion is formed between the inner peripheral surface of the distal end opening portion of the second tube body and the inner peripheral surface of the first tube body. The coating layer is disposed in the lumen of the first tube body and the lumen of the second tube body so as to coat the level difference portion. A thickness of a part of the coating layer, which covers the level difference portion, is larger than a thickness of the level difference portion.

In another aspect, the disclosed medical instrument includes a first tubular body comprising a lumen, a proximal end portion and an inner peripheral surface, the first tubular body extending in an axial direction. The medical instrument includes a second tubular body comprising a lumen, a distal end portion and an inner peripheral surface. The second tubular body is joined to the first tubular body by the distal end portion of the second tubular body being fitted into the proximal end portion of the first tubular body so that the first and second tubular bodies are integrally connected to one another. The inner peripheral surface of the distal end portion of the second tubular body is spaced apart from the inner peripheral surface of the proximal end portion of the first tubular body in a radial direction by a separation distance. A coating layer of a biocompatible material is on the inner peripheral surface of the first tubular body and on the inner peripheral surface of the second tubular body. The coating layer forms a continuous layer extending in the axial direction to cover the inner peripheral surfaces of the first and second tubular bodies. The thickness of the coating layer varies along an axial extent of the coating layer in the axial direction. The coating layer possesses a protrusion at a location where the inner peripheral surface of the second tubular body is spaced apart from the inner peripheral surface in the radial direction. The protrusion of the coating layer extends radially inward more than remaining portions of the coating layer. The thickness of the protrusion of the coating layer is greater than the separation distance between the inner peripheral surface of the second tubular body and the inner peripheral surface of the first tubular body.

Another aspect of the disclosure involves a method of manufacturing a medical instrument that includes applying a coating solution on an inner surface of one tubular body to form a protrusion on the inner surface of the one tubular body. The one tubular body possesses a lumen and a distal-most end. The protrusion of the coating solution is formed at the distal-most end of the one tubular body. The one tubular body includes a coating layer on the inner surface of the one tubular body before the applying of the coating solution. The method includes joining the one tubular body to another tubular body by inserting the distal-most end of the one tubular body into an open end of the other tubular body so that the distal-most end of the one tubular body is position in the other tubular body. The other tubular body has a coating layer on an inner surface of the other tubular body before the one tubular body is joined to the other tubular body. The lumen of the one tubular body directly communicates with the lumen of the other tubular body. The method includes bending the one tubular body relative to the other tubular body while the one tubular body is positioned in the other tubular body. The bending causes the coating solution to be applied to the inner surface of the other tubular body so that a continuous coating layer is created along the inner surfaces of the one tubular body and the other tubular body. The continuous coating layer is a biocompatible material that includes the coating solution, the coating layer on the one tubular body and the coating layer on the other tubular body.

According to the medical instrument having the above described configuration, even when the medical instrument is curved or the like and stress acts on the vicinity of the level difference portion, the coating layer is unlikely to be broken. Therefore, it is possible to help suitably suppress forming of a thrombus or the like in the vicinity of a joint portion between the first tube body and the second tube body.

DETAILED DESCRIPTION

Figure 3:
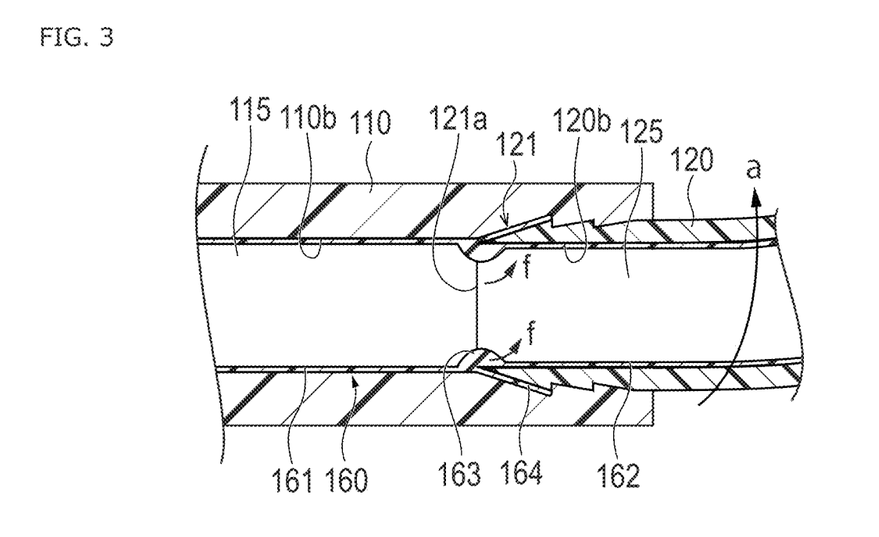
FIG. 3 is a sectional view for describing an example of an operation of the medical instrument.
Figure 4:
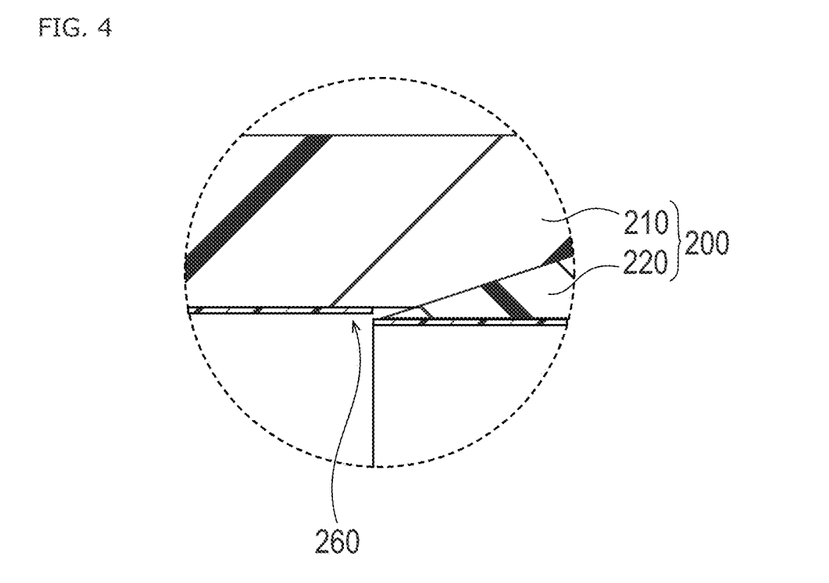
FIG. 4 is a sectional view for describing a medical instrument according to a comparative example.
Figure 5A:
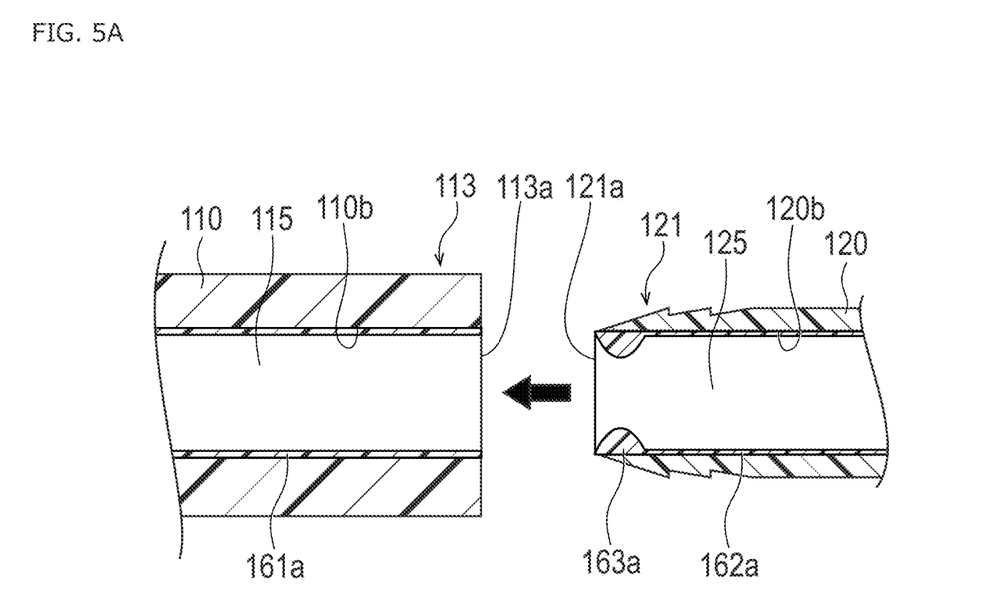
FIG. 5A is a sectional view showing a state when a first tube body and a second tube body are joined to each other according to the embodiment.
Figure 5B:
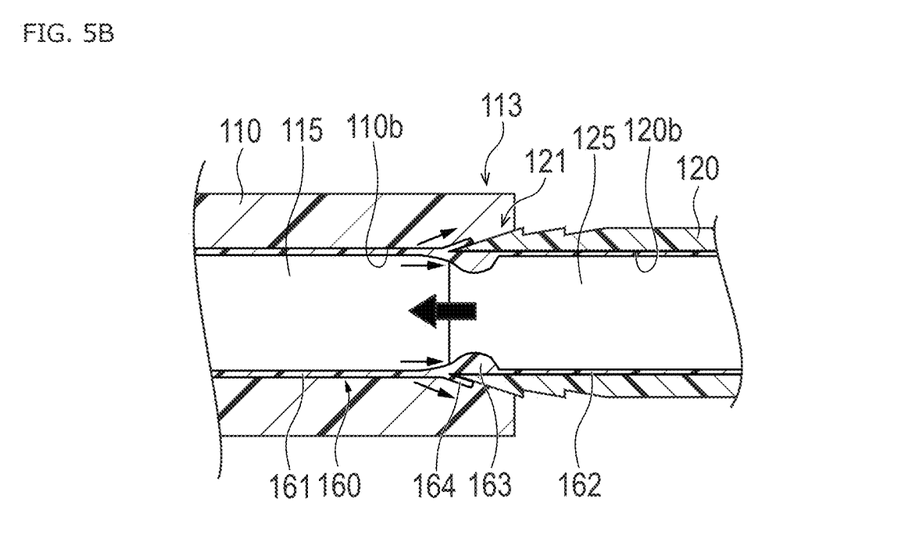
FIG. 5B is a sectional view showing a state when a distal end opening portion of the second tube body is inserted into the first tube body.

Set forth below is a detailed description of embodiments of a medical instrument and a method of manufacturing a medical instrument representing examples of the inventive medical instrument and method disclosed here. Hereinafter, a medical instrument 100 according to an embodiment will be described with reference to the figures. FIGS. 1A to 3 are views illustrating a configuration and an operation of the medical instrument 100, FIG. 4 is a view showing a medical instrument 200 according to a comparative example, and FIG. 5 is a view showing an example of a joining method (connecting method) of a first tube body 110 and a second tube body 120 of the medical instrument 100. A dimension ratio in the figures is enlarged depending on the description and the ratio is different from an actual ratio in some cases.

Figure 1A:
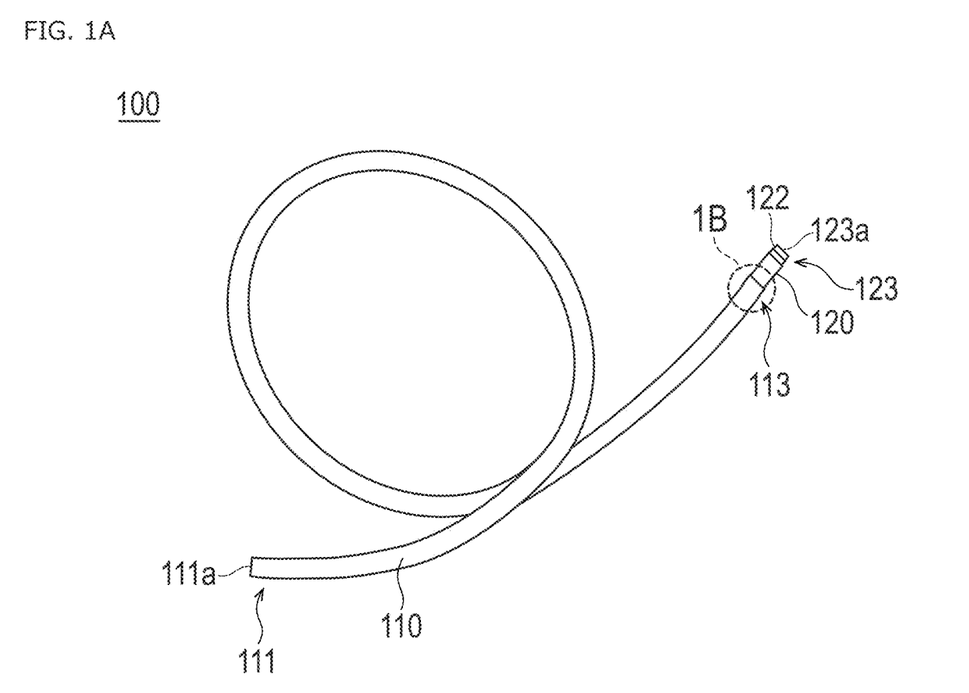
FIG. 1A is a view showing an overall configuration of a medical instrument according to an embodiment.
Figure 1B:
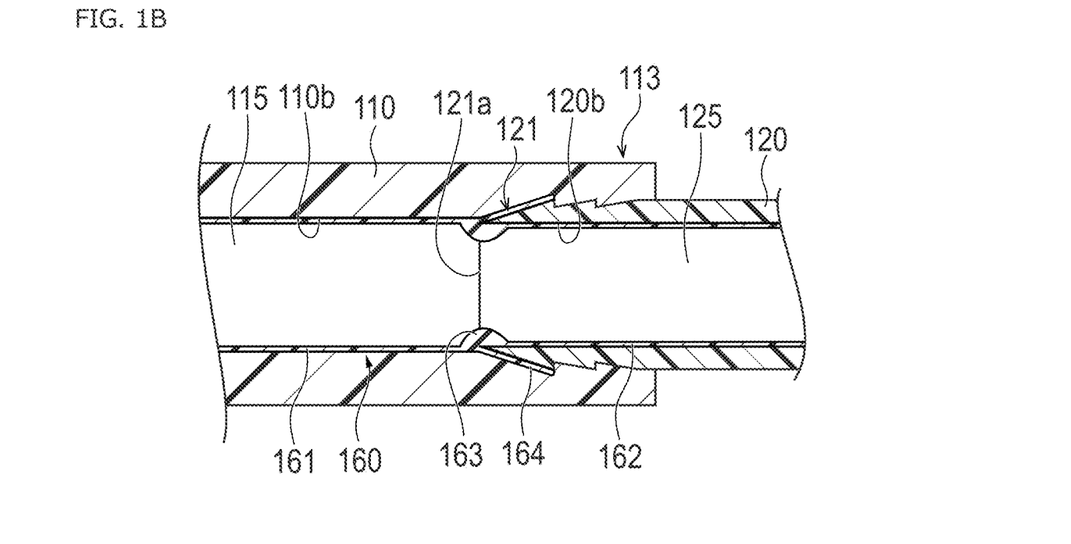
FIG. 1B is an enlarged sectional view in an axial direction of a part surrounded by dashed line portion 1B in FIG. 1A.

The medical instrument 100 according to the embodiment shown in FIGS. 1A and 1B is configured as a tube assembly that is used for transferring a body fluid or the like including blood. For example, the medical instrument 100 can be used as a part of an extracorporeal circulation circuit that is used in an artificial heart-lung system or the like.

As shown in FIGS. 1A and 1B, the medical instrument 100 includes the first tube body 110 that has a lumen 115, the second tube body 120 that has a lumen 125 and has rigidity higher than that of the first tube body 110 (i.e., the second tube body 120 is more rigid than the first tube body 110), and a coating layer 160 made of a biocompatible material. The coating layer 160 is disposed on an inner peripheral surface 110b of the first tube body 110 and an inner peripheral surface 120b of the second tube body 120.

The first tube body 110 is configured of an elongated tube-shaped member having flexibility (i.e., the first tube body 110 is a flexible elongated tubular member).

The first tube body 110 has a distal portion 111 (as shown in FIG. 1A) provided with a distal end opening portion 111a and a proximal portion 113 (as shown in FIGS. 1B and 5A) provided with a proximal end opening portion 113a. In other words, the first tube body 110 has an open distal end and an open proximal end. The lumen 115 of the first tube body 110 extends in an axial direction of the first tube body 110 so as to be continuous to the distal end opening portion 111a and the proximal end opening portion 113a.

In this description of the medical instrument, an end portion of the first tube body 110 where the first tube body 110 is joined to the second tube body 120 is referred to as the proximal portion 113, and an end portion positioned on the opposite side to the proximal portion 113 is referred to as the distal portion 111. However, the distal portion 111 and the proximal portion 113 of the first tube body 110 have substantially no difference in structure, and thus it is possible to use the distal portion 111 as the proximal portion and the proximal portion 113 as the distal portion. In addition, a direction (left-right direction in FIG. 1B), in which the first tube body 110 extends in a state in which no external force is applied, is referred to as the axial direction.

The second tube body 120 is configured as a medical connector that connects the first tube body 110 to another medical instrument (for example, a medical tube, a pump, various types of measuring instruments, a collection container, or the like).

The second tube body 120 has a distal portion 121 (as shown in FIGS. 1B and 5A) provided with a distal end opening portion 121a and a proximal portion 123 (as shown in FIG. 1A) provided with a proximal end opening portion 123a. The lumen 125 of the second tube body 120 extends in an axial direction of the second tube body 120 so as to be continuous to the distal end opening portion 121a and the proximal end opening portion 123a.

The first tube body 110 is joined to the second tube body 120 in a state in which the distal end opening portion 121a of the second tube body 120 is inserted into the lumen 115 of the first tube body 110 as illustrated in FIG. 1B. A predetermined range from the distal portion 121 of the second tube body 120 toward the side of the proximal end is inserted into the lumen 115 of the first tube body 110, thereby fitting the second tube body 120 in the first tube body 110 (i.e., a portion of the distal end of the second tube body 120 fits within the first tube body 110 as shown in FIG. 1B). In addition, the lumen 115 of the first tube body 110 and the lumen 125 of the second tube body 120 are coaxially disposed in a state in which both of the lumens 115, 125 communicate with each other.

A cross-sectional shape of the lumen 115 of the tube body 110 and a cross-sectional shape of the lumen 125 of the second tube body 120 are a circle (i.e., circular); however, the cross-sectional shape is not particularly limited and may be a rectangle, a triangle, an ellipse, or the like. The inner diameter and outer diameter of the first tube body 110 and the inner diameter and outer diameter of the second tube body 120 (as well as the other dimensions of the first and second tube bodies) are not particularly limited as long as the distal end opening portion 121a of the second tube body 120 is insertable (configured to be inserted) into the lumen 115 of the first tube body 110 at the proximal portion 113 of the first tube body 110 to thereby fit the second tube body 120 in the first tube body 110. In addition, the first tube body 110 does not need to be formed to have the constant inner diameter and constant outer diameter in the axial direction (i.e., the first tube body 120 can have an inner and/or outer diameter that varies over the axial extent of the first tube body 110). The second tube body 120 similarly does not need to be formed to have the constant inner diameter and outer diameter in the axial direction.

A level difference portion 150 and the coating layer 160 are described with reference to FIG. 2. In order to clearly show the level difference portion 150, the coating layer 160 is represented by a two-dot chain line in FIG. 2.

Figure 2:
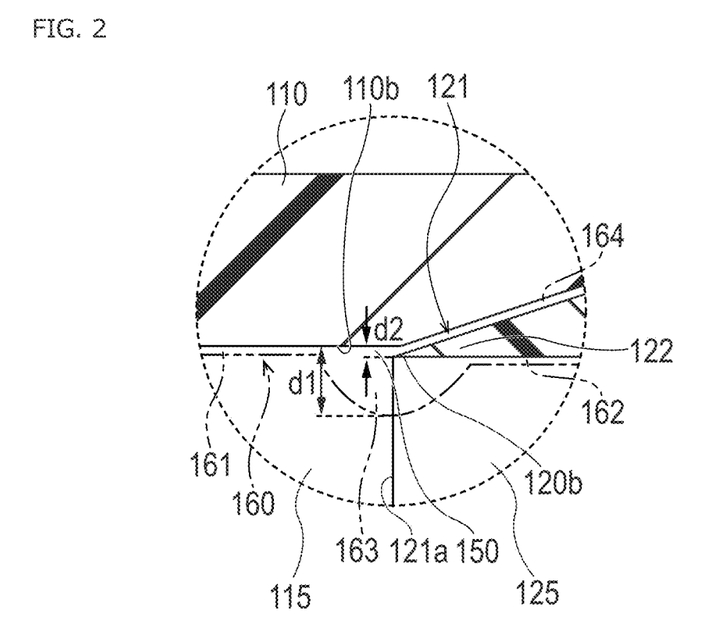
FIG. 2 is a sectional view illustrating an example of a relationship between the thickness of a level difference portion and the thickness of a coating layer that coats the level difference portion of the medical instrument.

As shown in FIG. 2, the level difference portion 150 is formed between the inner peripheral surface of the distal end opening portion 121a of the second tube body 120 (the inner peripheral surface 120b of the second tube body 120) and the inner peripheral surface 110b of the first tube body 110. That is, the inner peripheral surface 120b of the second tube body 120 is radially inward of the inner peripheral surface 110b of the first tube body 110 to create the level difference portion.

The coating layer 160 is disposed in the lumen 115 of the first tube body 110 and the lumen 125 of the second tube body 120 (i.e., along the inner surfaces of the first tube body 110 and the second tube body 120) so as to coat the level difference portion 150.

The coating layer 160 has a first region 161 disposed in the lumen 115 of the first tube body 110, a second region 162 disposed in the lumen 125 of the second tube body 120, a third region 163 that is disposed between the first region 161 and the second region 162 in the axial direction, and a fourth region 164 interposed between the inner peripheral surface 110b of the first tube body 110 and an outer peripheral surface of a tapered portion 122 of the second tube body 120. The third region 163 of the coating layer 160 covers the level difference portion 150 (corresponding to a part of the coating layer 160 which covers the level difference portion 150) as shown in FIGS. 2 and 3.

There is no clear boundary between the regions 161, 162, 163, and 164—the coating layer 160 is continuously formed on the inner peripheral surface 110b of the first tube body 110 and the inner peripheral surface of the distal end opening portion 121a of the second tube body 120, in the state in which the distal end opening portion 121a of the second tube body 120 is inserted into the lumen 115 of the first tube body 110. In addition, the distal end of the first region 161 extends to the distal end opening portion 111a of the first tube body (e.g., refer to FIG. 1A), and the proximal end of the second region 162 extends to the proximal end opening portion 123a of the second tube body 120 (e.g., refer to FIG. 1A).

As shown in FIG. 2, a thickness d1 of the third region in a radial direction (up-down direction in FIG. 2), which is orthogonal to the axial direction of the first tube body 110 and the second tube body 120, is formed to be larger than a thickness d2 of the level difference portion 150. Preferably, the thickness d1 of the coating layer 160 is the thickness of the coating layer 160 at a cross section orthogonal to the axial direction of the first tube body 110 and the second tube body 120 (i.e., the radial direction) at the most distal end of the second tube body 120. The thickness d2 of the level difference portion 150 is a length (distance) between the inner peripheral surface 110b of the first tube body 110 and the inner peripheral surface 120b of the second tube body 120 at the cross section orthogonal to the axial direction of the first tube body 110 and the second tube body 120 (radial direction) on the most distal end of the second tube body 120.

The third region 163 of the coating layer 160 forms a convex portion (e.g., a protrusion) at the level difference portion 150. For example, the convex portion of the coating layer 160 can be formed to have a cross-sectional shape which is curved into a convex shape protruding toward the axial core (an inward side in the radial direction) of the tube bodies 110 and 120 as shown in FIG. 2. Forming the cross-sectional shape into a convex shape protruding radially inward can help reduce a possibility of breaking the coating layer 160 in the vicinity of the level difference portion 150. Therefore, blood or the like can smoothly flow even in the vicinity of the third region 163, and it is possible to suitably prevent flowing of the blood from being stagnant in the vicinity of the level difference portion 150 and thrombus from being formed. Note that, the cross-sectional shape of the third region 163 has a certain extent of length in the axial direction (i.e., axial extent), and it is more preferable to have a gently curved shape (for example, a streamline shape) in the axial direction; however, the shape is not limited.

The thickness d1 of the third region can be, for example, 0.5 mm to 2 mm when the thickness d2 of the level difference portion 150 is 0.1 mm to 1 mm. However, the thickness d1 of the third region is not particularly limited as long as the thickness d1 of the third region is larger than the thickness d2 of the level difference portion 150. In addition, a length dimension (dimension in the axial direction) of the third region is not particularly limited as the third region coats (i.e., covers or overlaps in the axial direction) the level difference portion 150. In addition, thicknesses of the other regions 161, 162, and 164 of the coating layer 160 are not particularly limited and can be formed to have any dimensions.

Note that, in the embodiment illustrated in FIG. 1B, "to cover the level difference portion with the coating layer (third region)" means that a part of the coating layer 160 is disposed to fill the level difference portion (gap) 150 formed between the inner peripheral surface 110b of the first tube body 110 and the inner peripheral surface 120b of the second tube body 120, thereby forming a state in which both of the lumens 115 and 125 of the tube bodies 110 and 120 do not directly communicate with the level difference portion 150 (i.e., blood in the lumens 115, 125 will directly contact the coating layer 160 instead of reaching the level difference portion 150).

The thickness of the first region 161 of the coating layer 160 disposed on the inner peripheral surface 110b of the first tube body 110 may be larger than the thickness of the second region 162 of the coating layer 160 disposed on the inner peripheral surface 120b of the second tube body 120. Based on this configuration, the coating layer 160 can simply cover the level difference portion 150 between the first and second regions 161, 162 of the coating layer 160. Specific dimensions of the thickness of the first region 161 and the thickness of the second region 162 are not particularly limited as long as the coating layer 160 can cover the level difference portion 150.

As shown in FIG. 2, the distal portion 121 of the second tube body 120 forms the tapered portion 122 in which the outer peripheral surface is inclined from a proximal side to a distal side (i.e., the distal end of the second tube body 120 is tapered as shown in FIG. 2 with an outer diameter that increases in the proximal direction from the distal tip). In other words, the tapered portion 122 is formed to have a shape that is tapered toward the distal side of the second tube body 120.

The fourth region 164 of the coating layer 160 is interposed between the inner peripheral surface 110b of the first tube body 110 and the outer peripheral surface of the tapered portion 122 when the distal end opening portion 121a of the second tube body 120 is inserted into the lumen 115 of the first tube body 110 (a state in which the first tube body 110 and the second tube body 120 are joined to each other).

The second tube body 120 has a plurality of tapered portions proximal to the tapered portion 122. The tapered portion 122 and the tapered portions formed proximal to the tapered portion 122 improve the insertability of the second tube body 120 into the lumen 115 of the first tube body 110 (i.e., the second tube body 120 is relatively easier to insert based on the tapered portions). In addition, the distal portion 121 of the second tube body 120 forms the tapered portion 122, and thereby it is possible to reduce the thickness of the distal portion 121 of the second tube body 120 (i.e., the wall thickness of the second tube body 120 at the distal end of the second tube body 120). Therefore, it is possible to reduce the thickness d2 of the level difference portion 150 formed between the inner peripheral surface 110b of the first tube body 110 and the inner peripheral surface of the distal end opening portion 121a of the second tube body 120.

The specific cross-sectional shape, size, and the like of the tapered portion 122 are not particularly limited. It is also possible to provide the tapered portion 122 and a plurality of other tapered portions on the proximal portion 123 of the second tube body 120 as shown in FIG. 1A.

Materials of the first tube body 110, the second tube body 120, and the coating layer 160 are described next.

The material of the first tube body 110 and the second tube body 120 is not particularly limited. It is possible to use the same material as the material used for a common tube body (for example, a tube, a connector, or the like). Specifically, examples of the material of the first tube body 110 and/or the second tube body 120 include polyvinyl chloride; polycarbonate; polyvinylidene chloride (PVDC); a polyolefin or a modified polyolefin such as polyethylene, polypropylene, or ethylene-α-olefin copolymers; polystyrene; polyamide; polyimide; polyimide-imides; polyurethane; polyester such as polyethylene terephthalate (PET), polybutylene terephthalate (PBT), polycyclohexane terephthalate, or polyethylene-2,6-naphthalate; fluororesin such as polytetrafluoroethylene (PTFE), an ethylene-tetrafluoroethylene copolymer (ETFE), a tetrafluoroethylene perfluoroalkyl vinyl ether copolymer (PFA), or polyvinylidene fluoride; polyether; aromatic polyether ketone such as polyether ketone (PEK) or polyether ether ketone (PEEK); polyetherimide; ABS resin (acrylonitrile-butadiene-styrene copolymer resin); AS resin (a acrylonitrile-styrene copolymer); a butadiene-styrene copolymer; acrylic resin; polymethylmethacrylate; polyacetal (POM); polyphenylene oxide; modified polyphenylene oxide; polysulfone; polyethersulfone; polyphenylene sulfide; polyarylate; aromatic polyester (liquid crystal polymer); polyimide-based thermoplastic elastomer; an ethylene-vinyl acetate copolymer (EVA); poly-(4-methylpentene-1); ionomer; silicone rubber; or the like. In addition, a blend, a polymer alloy, or the like containing one or more selected from the materials described above may be used. In addition to those described above, various types of glass materials, ceramic materials, or metal materials may be used.

The first tube body 110 and the second tube body 120 may be formed of the same material as each other or may be formed of different materials from one another. However, the second tube body 120 has rigidity higher than that of the first tube body 110 (i.e., the second tube body 120 is relatively more rigid than the first tube body 110). The rigidity of the first tube body 110 and the rigidity of the second tube body 120 are set so that the first tube body 110 and the second tube body 120 are brought into close contact with each other and fit to one another. It is thus possible to increase a joining force of both of the tube bodies 110 and 120.

The first tube body 110 and the second tube body 120 (particularly the first tube body 110) are preferably substantially transparent. An operator can thus easily and reliably visually recognize a state (for example, flowing or color) of a transferred substance (for example, blood) through the first tube body 110. Combinations of the first tube body 110 and the second tube body 120 materials are not particularly limited, and those skilled in the art can appropriately select the respective materials and the combination of materials. Examples of a combination of materials used to form the first tube body 110 and the second tube body 120 include a combination of soft polyvinyl chloride and polycarbonate, a combination of soft polyvinyl chloride and hard polyvinyl chloride, a combination of a resin material and a metal material, a combination of a resin material and a ceramic material, or a combination of a resin material and a glass material.

The coating layer 160 biocompatible material is not particularly limited as long as the biocompatible material has biocompatibility (particularly, antithrombotic). It is possible to use a known material in the same manner. Examples of biocompatible materials can include polyalkoxyalkyl (meth)acrylate, polyalkylene glycol, polyalkyl(meth)acrylamide, polyvinylpyrrolidone, mucopolysaccaride (for example, heparin, hyaluronic acid, chondroitin sulfate, dextran sulfate, keratan sulfate, heparan sulfate, dermatan sulfate, a derivative thereof (for example, heparin salt such as heparin sodium, heparin potassium, or heparin calcium, or epoxidized heparin) or the like), an artificial heparinoid which is a hydrophilic polymer having a sulfo group and a derivative thereof (for example, poly(2-acrylamido-2-methylpropanesulfonic acid) or polyvinyl sulfate), elastin, or the like. The material described above may be used by one or may be used as a combination of two or more selected from the materials.

The coating layer 160 may be formed without being chemically bonded to the inner peripheral surface 110b of the first tube body 110 and the inner peripheral surface 120b of the second tube body 120. In this case, a molecular weight of the coating layer (biocompatible material) 160 is not particularly limited as long as desired biocompatibility (particularly, the antithrombotic) is obtained. When the inner peripheral surface 110b of the first tube body 110 and the inner peripheral surface 120b of the second tube body 120 are formed of a hydrophobic material, it is preferable that the coating layer 160 is made of a hydrophobic material that has the biocompatibility and a weight-average molecular weight of 400,000 or heavier, more preferably 500,000 or heavier and 1,000,000 or lighter. For example, the hydrophobic material having the desired biocompatibility may be poly(2-methoxyethyl acrylate) (PMEA) having the antithrombotic. The weight-average molecular weight of the coating layer 160 is regulated as described above and the coating layer 160 is formed to have relatively high viscosity, and thus the coating layer 160 is unlikely to shift or peel. Further, it is possible to easily perform coating with the coating layer 160 (i.e., apply the coating layer 160 to the inner surface of the first and second tube bodies 110, 120), and the coating layer 160 can be more strongly attached fixed to a surface of the first tube body 110 or the second tube body 120. In addition to this, it is possible to improve durability more uniformly and with respect to blood since the cohesion force of the biocompatible material is improved.

Next, an operation at the third region 163 of the coating layer 160 is described.

For example, when deformation such as curvature, twist, or the like (as represented by an arrow "a" as shown in FIG. 3) occur in a state in which the first tube body 110 and the second tube body 120 are joined to each other, stress "f" acts in the vicinity of the level difference portion 150. Since the fracture resistance of the coating layer 160 according to the embodiment locally increases in the vicinity of the third region 163 that covers the level difference portion 150, it is possible to help prevent the coating layer 160 from being broken (ruptured) in the vicinity of the level difference portion 150 even in a case where the stress "f" or the like acts thereon.

FIG. 4 shows a medical instrument 200 according to a comparative example.

The comparative example of FIG. 4 shows a medical instrument 200 that has a coating layer 260 that is not more thick (i.e., does not possess a thickness larger than the thickness of a level difference portion 250) than the level difference portion 250. In this comparative example, the coating layer 260 is relatively easily broken when deformation such as bending occurs in the medical instrument 200. When the coating layer 260 is broken, a gap is formed between an inner peripheral surface of a first tube body 210 and an outer peripheral surface of a second tube body 220 and blood flow or the like may stagnate around the gap. Therefore, a thrombus (blockage) is relatively more likely to be formed. In contrast to the comparative example of FIG. 4, the medical instrument 100 shown in FIGS. 1A-3 is capable of suitably preventing the coating layer 160 from being broken in the vicinity of the level difference portion 150 (as described above), and thus it is possible to prevent the thrombus from being formed (i.e., which is formed due to the break of the coating layer 260).

Next, an example of a work procedure of joining the first tube body 110 and the second tube body 120 to each other is described.

As shown in FIG. 5A, a part 161a constituting the first region 161 of the coating layer 160 is disposed on the inner peripheral surface 110b of the first tube body 110 in advance before joining the first tube body 110 and the second tube body 120 to one another. On the other hand, a part 162a constituting the second region 162 of the coating layer 160 and a part 163a constituting the third region 163 of the coating layer 160 are disposed on the inner peripheral surface 120b of the second tube body 120 in advance before joining the first tube body 110 and the second tube body 120 to one another.

After both of the tube bodies 110 and 120 are prepared as described above, the distal end opening portion 121a of the second tube body 120 is inserted into the lumen 115 of the first tube body 110 via the proximal end opening portion 113a of the first tube body 110 (i.e., the distal end of the second tube body 120 is inserted into the open proximal end of the first tube body 110).

When the second tube body 120 is pushed into the lumen 115 of the first tube body 110, the part 161a constituting the first region 161 of the coating layer 160 and the part 163a constituting the third region 163 of the coating layer 160 come into contact with each other and are united while being mixed together to form a continuous portion of the coating layer 160 as shown in FIG. 5B. When the pushing work is performed (i.e., when the second tube body 120 is pushed/inserted into the lumen 115 of the first tube body), a part of the coating layer 160 enters a space (gap) between the inner peripheral surface 110b of the first tube body 110 and the outer peripheral surface of the tapered portion 122 of the second tube body 120, and thereby the fourth region 164 of the coating layer 160 is formed. When the second tube body 120 is pushed further into the lumen 115 of the first tube body 110, and the second tube body 120 becomes inserted by a predetermined length (i.e., a certain length in the axial direction), the second tube body 120 is fitted in the first tube body 110 such that both of the tube bodies 110 and 120 are joined to each other (i.e., so that the first and second tube bodies 110 and 120 move together as an integral structure).

The medical instrument 100 described above and shown in FIGS. 1A-3 includes the first tube body 110 that has a lumen 115, the second tube body 120 that has a lumen 125 and is more rigid than the first tube body 110, and the coating layer 160 made of the biocompatible material. The biocompatible coating layer 160 is disposed on the inner peripheral surface 110b of the first tube body 110 and the inner peripheral surface 120b of the second tube body 120. When the distal end opening portion 121a of the second tube body 120 is inserted into the lumen 115 of the first tube body 110, the first tube body 110 is joined to the second tube body 120, and the level difference portion 150 is formed between the inner peripheral surface 110b of the first tube body 110 and the inner peripheral surface of the distal end opening portion 121a of the second tube body 120. The coating layer 160 is disposed in the lumen 115 of the first tube body 110 and the lumen 125 of the second tube body 120 (i.e., on the inner surfaces of the first and second tube bodies 110, 120) so as to cover the level difference portion 150. The thickness d1 of a part (third region 163) of the coating layer 160, which covers the level difference portion 150, is formed to be larger than the thickness d2 of the level difference portion 150.

According to the medical instrument 100 having the above-described configuration, even when the medical instrument 100 is curved or the like and the stress acts on the vicinity of the level difference portion 150, the coating layer 160 is unlikely to be broken (i.e., relatively less likely to break), and thus it is possible to suitably suppress forming of the thrombus or the like in the vicinity of a joint portion between the first tube body 110 and the second tube body 120.

The thickness of the coating layer 160 on the inner peripheral surface 110b of the first tube body 110 is larger than the thickness of the coating layer 160 on the inner peripheral surface 120b of the second tube body 120. Therefore, the coating layer 160 can simply cover the vicinity of the level difference portion 150, and it is possible to improve the fracture resistance of the coating layer 160 in the vicinity of the level difference portion 150.

The coating layer 160 includes the convex portion at the level difference portion 150. Therefore, it is possible to improve the fracture resistance of the coating layer 160 in the vicinity of the level difference portion 150.

The distal portion 121 of the second tube body 120 forms the tapered portion 122 in which the outer peripheral surface is inclined from the proximal side to the distal side (i.e., the distal portion 121 of the second tube body 120 tapers towards the distal end). The coating layer 160 is interposed between the inner peripheral surface 110b of the first tube body 110 and the outer peripheral surface of the tapered portion 122 when the distal end opening portion 121a of the second tube body 120 is inserted into the lumen 115 of the first tube body 110. In this manner, an area of a surface of the coating layer 160 that is brought into contact with the first tube body 110 and the second tube body 120 is increased. The coating layer 160 is unlikely to shift or the like even when deformation such as bending occurs in the medical instrument 100 because a part of the coating layer 160 is between (i.e., sandwiched between) the inner peripheral surface 110b of the first tube body 110 and the outer peripheral surface of the tapered portion 122. Therefore, it is possible to more suitably prevent the coating layer 160 from being broken.

The coating layer 160 is continuously formed on the inner peripheral surface 110b of the first tube body 110 and the inner peripheral surface of the distal end opening portion 121a of the second tube body 120, in the state in which the distal end opening portion 121a of the second tube body 120 is inserted into the lumen 115 of the first tube body 110. Therefore, it is possible to further improve the fracture resistance of the entire coating layer 160.

The coating layer 160 is formed of a biocompatible material that is an antithrombotic material, so that it is possible to suitably prevent the thrombus from being formed on the inner peripheral surface 110b of the first tube body 110 and the inner peripheral surface 120b of the second tube body 120.

The coating layer 160 is not chemically bonded to the inner peripheral surface 110b of the first tube body 110 made of the hydrophobic material and the inner peripheral surface 120b of the second tube body 120 made of the hydrophobic material. The coating layer 160 has hydrophobicity (i.e., is relatively hydrophobic) and is formed of the antithrombotic material having the weight-average molecular weight of 400,000 or heavier. Preferably, the antithrombotic material is poly(2-methoxyethyl acrylate) (PMEA) having the antithrombotic. When this configuration is employed, the coating layer 160 is formed to have relatively high viscosity, and thus the coating layer 160 is unlikely to shift or peel even when the coating layer 160 is not chemically bonded to the inner peripheral surface 110b of the first tube body 110 and the inner peripheral surface 120b of the second tube body 120. Accordingly, it is possible to suitably maintain the function of the coating layer 160 over a long term (i.e., a relatively long amount of time).

The advantageous effects of the disclosed medical instrument are described by using the following example and comparative example. However, the scope of the disclosed medical instrument is not limited to only the following examples. Note that, in the following example, an operation is performed at room temperature (25° C.). Unless otherwise specified, "%" and "part" mean "% by weight" and "part by weight", respectively.

Example

1. PMEA (weight-average molecular weight=600,000) was dispersed in methanol such that the concentration of PMEA was 0.1% by weight, and a coating solution (1) was prepared.

2. PMEA (weight-average molecular weight=600,000) was dispersed in methanol such that the concentration of PMEA was 30% by weight, and a coating solution (2) was prepared.

3. After the inner peripheral surface of the first tube body (a soft polyvinyl chloride tube having an inner diameter of 9.5 mm) was dip-coated with the coating solution (1) (prepared as described above) at room temperature for ten seconds, the coated first tube body was raised and remained still to be dried at room temperature for 24 hours.

4. After the inner peripheral surface of the second tube body (a polycarbonate straight connector having an inner diameter of 10 mm) was immersed (dipped) in the coating solution (1) (prepared as described above) at room temperature for ten seconds, the coated second tube body was raised and remained still to be dried at room temperature for 24 hours.

5. Next, after the distal portion of the second tube body (the vicinity of the distal end opening portion) was immersed (dipped) for ten seconds in the coating solution (2) prepared as described above, the coated second tube body was raised, positioned in an oven heated to 40° C., and dried. The operation was repeated three times, and the part 163a (refer to FIG. 5(A)) constituting the third region of the coating layer was formed on the second tube body.

6. The distal end opening portion of the second tube body was inserted into the lumen of the first tube body, and the third region 163 was formed on the coating layer (as shown in FIG. 5B). Then, the vicinity of the level difference portion (the vicinity of the joint portion) was curved (i.e., flexed or bent) ten times in a direction (up-down direction) symmetrical about a bending angle of 45°, with an axial core of the first tube body and the second tube body as a reference. A sample (1) was prepared in accordance with such a procedure described above.

Comparative Example

1. PMEA (weight-average molecular weight=600,000) was dispersed in methanol such that the concentration of PMEA was 0.1% by weight, and a coating solution (1) was prepared.

2. After the inner peripheral surface of the first tube body (a soft polyvinyl chloride tube having an inner diameter of 9.5 mm) was dip-coated with the coating solution (1) (prepared as described above) at room temperature for ten seconds, the coated first tube body was raised and remained still to be dried at room temperature for 24 hours.

3. After the inner peripheral surface of the second tube body (a polycarbonate straight connector having an inner diameter of 10 mm) was immersed (dipped) in the coating solution (1) (prepared as described above) at room temperature for ten seconds, the coated second tube body was raised and remained still to be dried at room temperature for 24 hours.

4. The distal end opening portion of the second tube body was inserted into the lumen of the first tube body. Then, the vicinity of the level difference portion (the vicinity of the joint portion) was curved (i.e., flexed or bent) ten times in a direction (up-down direction) symmetrical about a bending angle of 45°, with the axial core of the first tube body and the second tube body as a reference. A sample (2) was prepared in accordance with such a procedure described above.

[Antithrombotic Test]

The antithrombotic test was conducted on the samples (1) and (2) prepared as described above in accordance with the following method.

Figure 6:
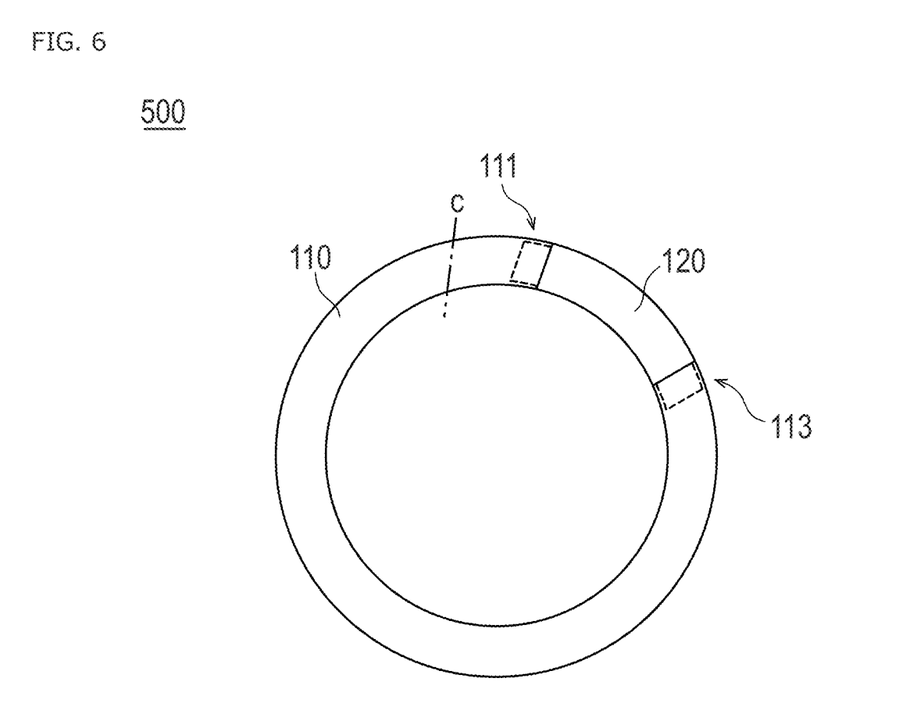
FIG. 6 illustrates an outline of a thrombogenicity test.

After the lumens of the samples were filled with swine fresh blood (circulation blood) to which heparin was added such that the concentration of heparin in the blood was 1 unit/ml, both end portions of the second tube body 120 were inserted into and were joined to both of the end portions 111 and 113 of the first tube body 110, as shown in FIG. 6, and a blood circulation circuit 500 was formed. A blood circulation circuit 500 was fixed to a cylindrical rotating device and rotation (circulation) was performed at 20 rpm for two hours.

After the circulation of the swine fresh blood under such conditions described above was ended, the first tube body 110 was cut at a cutting portion "c" shown in FIG. 6 (the position of the cut can be at any position other than at the joint portion). The cut portion is then cleaned with a physiological solution (saline), and the vicinity of the level difference portion (the vicinity of the joint portion) of the first tube body 110 and the second tube body 120 was observed.

Figure 7:
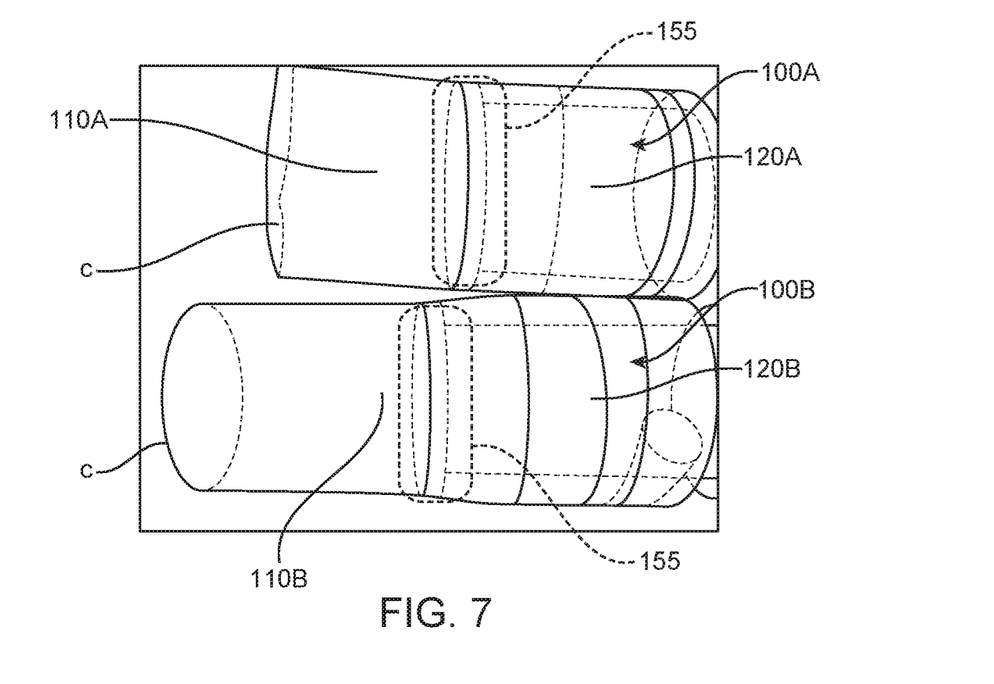
FIG. 7 is an enlarged photograph of a medical instrument according to an example.
Figure 8:
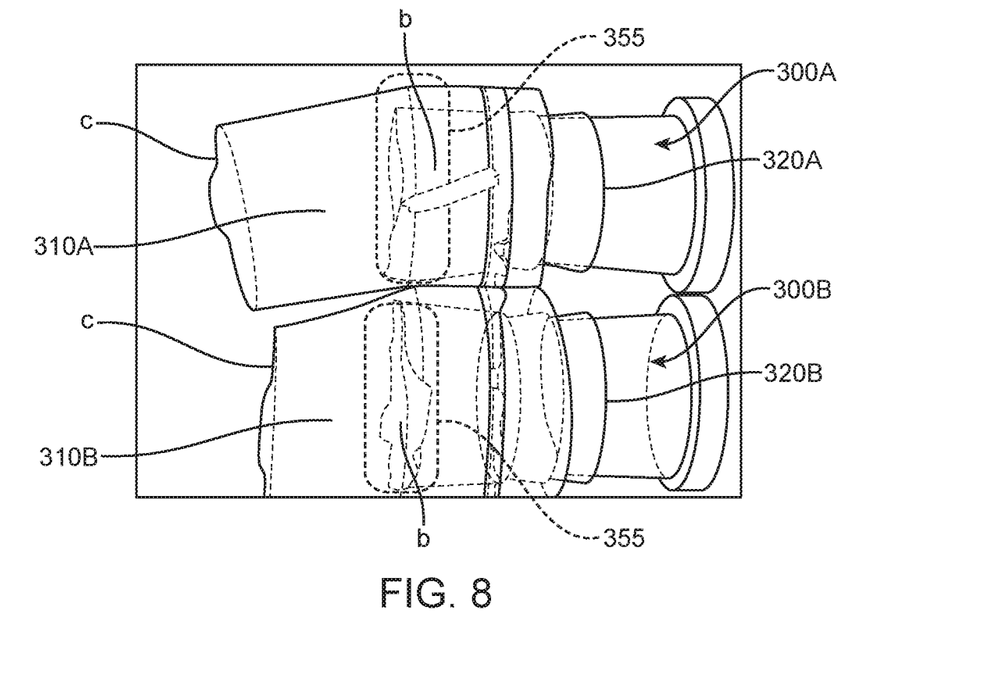
FIG. 8 is an enlarged photograph of the medical instrument according to the comparative example.

FIG. 7 shows test results of the sample in the example, and FIG. 8 shows test results of the sample of the comparative example. FIG. 7 is a photograph of the medical instrument 100 after the antithrombotic test and a photograph obtained by enlarging and imaging a vicinity 155 of the level difference portion (a vicinity of the joint portion). FIG. 8 is a photograph of a medical instrument 300 after the antithrombotic test and a photograph obtained by enlarging and imaging a vicinity 355 of a level difference portion (vicinity of a joint portion).

In the example, the antithrombotic test was conducted on two samples of a medical instrument 100A having a first tube body 110A and a second tube body 120A and a medical instrument 100B having a first tube body 110B and a second tube body 120B. The antithrombotic test was also conducted on two samples of a medical instrument 300A having a first tube body 310A and a second tube body 320A and a medical instrument 300B having a first tube body 310B and a second tube body 320B in the comparative example.

The results shown in FIG. 7 illustrate that few thrombi were formed in the vicinity 155 of the level difference portion of each of the medical instruments 100A and 100B which were the samples of the example. The results shown in FIG. 8, however, illustrate that many (relatively more) thrombi b (less bright parts in FIG. 8) were formed in the vicinity 355 of the level difference portion of each of the medical instruments 300A and 300B which were the samples of the comparative example, compared to the example.

The results described above demonstrate that each of the medical instruments 100A and 100B that were provided with the third region 163 of the coating layer 160 covering the level difference portion 150 more satisfactorily suppressed forming of the thrombus in the vicinity of the level difference portion 150.

The medical instrument is described above in relation to particular embodiment(s); however, the inventive medical instrument is not limited to the configuration described in any particular embodiment(s), and it is possible to perform appropriate modifications, e.g., based on below claims.

For example, the medical instrument described above and illustrated in FIGS. 1A-5B has the hollow tube-shaped first tube body and the hollow second tube body having the function of the connector; however, a structure of each of the tube bodies is not particularly limited as long as the second tube body is inserted into the first tube body, thereby making it possible to join (connect) the tube bodies to each other. The specific shape or the like of the tube bodies described above and illustrated in the figures may be appropriately changed. In addition, the use of the medical instrument is not particularly limited as long as the medical instrument is used for transferring the blood.

In other embodiments, the coating layer may be disposed to cover at least the level difference portion in the lumen of the first tube body and the lumen of the second tube body, may not be formed along the entire length of the lumen of the first tube body in the axial direction, or may not be formed along the entire length of the lumen of the second tube body in the axial direction.

The detailed description above describes a medical instrument and a method of manufacturing a medical instrument. The invention is not limited, however, to the precise embodiments and variations described. Various changes, modifications and equivalents can be effected by one skilled in the art without departing from the spirit and scope of the invention as defined in the accompanying claims. It is expressly intended that all such changes, modifications and equivalents which fall within the scope of the claims are embraced by the claims.

What is claimed is:

1. A medical instrument comprising:
a first tube body that has a lumen and an inner peripheral surface, the first tube body extending in an axial direction;
a second tube body that has a lumen, an inner peripheral surface and an open distal end, the second tube body being more rigid than the first tube body;
a coating layer made of a biocompatible material, the coating layer being disposed on the inner peripheral surface of the first tube body and on the inner peripheral surface of the second tube body;
the first tube body being joined to the second tube body by the open distal end of the second tube body being inserted into the lumen of the first tube body;
a level difference portion being formed between the inner peripheral surface of the open distal end of the second tube body and the inner peripheral surface of the first tube body, the inner peripheral surface of the second tube body being radially inward of the inner peripheral surface of the first tube body to create the level difference portion, the level difference portion possessing a thickness, the thickness of the level difference portion being a distance between the inner peripheral surface of the second tube body and the inner peripheral surface of the first tube body;
the coating layer in the lumen of the first tube body extending to the lumen of the second tube body so that a part of the coating layer coats the level difference portion, the coating layer possessing a thickness, the thickness of the coating layer which coats the level difference portion being a distance between the inner peripheral surface of the first tube body and an inner peripheral surface of the coating layer on the level difference portion; and
the thickness of the part of the coating layer which coats the level difference portion is greater than the thickness of the level difference portion.

2. The medical instrument according to claim 1, wherein the thickness of the coating layer disposed on the inner peripheral surface of the first tube body is larger than the thickness of the coating layer disposed on the inner peripheral surface of the second tube body.

3. The medical instrument according to claim 1, wherein the part of the coating layer that coats the level difference portion is a convex protrusion that protrudes radially inward from the level difference portion.

4. The medical instrument according to claim 1, wherein the open distal end of the second tube body has a tapered outer surface which is inclined from a largest outer diameter on a proximal side to a smallest outer diameter on a distal side in the axial direction.

5. The medical instrument according to claim 4, wherein the coating layer is interposed between the inner peripheral surface of the first tube body and the tapered outer surface of the open distal end of the second tube body.

6. The medical instrument according to claim 1, wherein the coating layer is continuously formed on the inner peripheral surface of the first tube body and the inner peripheral surface of the distal end opening portion of the second tube body.

7. The medical instrument according to claim 1, wherein the biocompatible material is an antithrombotic material.

8. The medical instrument according to claim 7, wherein
the inner peripheral surface of the first tube body is made of a hydrophobic material and the inner peripheral surface of the second tube body is made of a hydrophobic material,
the coating layer is not chemically bonded to the inner peripheral surfaces of the first and second tube bodies, and
the coating layer has hydrophobicity and is formed of the antithrombotic material having a weight-average molecular weight of 400,000 or heavier.

9. A medical instrument comprising:
a first tubular body comprising a lumen, a proximal end portion and an inner peripheral surface, the first tubular body extending in an axial direction;
a second tubular body comprising a lumen, a distal end portion and an inner peripheral surface, the second tubular body being joined to the first tubular body by the distal end portion of the second tubular body being fitted into the proximal end portion of the first tubular body so that the first and second tubular bodies are integrally connected to one another;
the inner peripheral surface of the distal end portion of the second tubular body being spaced apart from the inner peripheral surface of the proximal end portion of the first tubular body in a radial direction by a separation distance;
a coating layer of a biocompatible material on the inner peripheral surface of the first tubular body and on the inner peripheral surface of the second tubular body, the coating layer forming a continuous layer extending in the axial direction to cover the inner peripheral surfaces of the first and second tubular bodies, the coating layer possessing a thickness; and
the thickness of the coating layer varying along an axial extent of the coating layer in the axial direction, the coating layer possessing a protrusion at a location where the inner peripheral surface of the second tubular body is spaced apart from the inner peripheral surface in the radial direction, the protrusion of the coating layer extending radially inward more than remaining portions of the coating layer; and
the thickness of the protrusion of the coating layer being greater than the separation distance between the inner peripheral surface of the second tubular body and the inner peripheral surface of the first tubular body.

10. The medical instrument according to claim 9, wherein the second tubular body is more rigid than the first tubular body.

11. The medical instrument according to claim 9, wherein the thickness of the coating layer on the inner peripheral surface of the first tubular body distal to the protrusion is greater than the thickness of the coating layer on the inner peripheral surface of the second tubular body proximal to the protrusion.

12. The medical instrument according to claim 9, wherein
the second tubular body possesses a distal tip; and
the distal end portion of the second tubular body has a tapered outer surface which is inclined in the axial direction towards a smallest outer diameter at the distal tip of the second tubular body.

13. The medical instrument according to claim 9, wherein the protrusion of the coating layer has a different composition in at least one respect than the remaining portions of the coating layer.

14. A medical instrument comprising:
a first tube body that has a lumen and an inner peripheral surface, the first tube body extending in an axial direction;
a second tube body that has a lumen, an inner peripheral surface and an open distal end, the second tube body being more rigid than the first tube body;
a coating layer made of a biocompatible material, the coating layer being disposed on the inner peripheral surface of the first tube body and on the inner peripheral surface of the second tube body;
the first tube body being joined to the second tube body by the open distal end of the second tube body being inserted into the lumen of the first tube body;
a level difference portion being formed between the inner peripheral surface of the open distal end of the second tube body and the inner peripheral surface of the first tube body, the inner peripheral surface of the second tube body being radially inward of the inner peripheral surface of the first tube body to create the level difference portion, the level difference portion possessing a thickness;
the coating layer in the lumen of the first tube body extending to the lumen of the second tube body so that a part of the coating layer coats the level difference portion, the coating layer possessing a thickness; and
wherein the thickness of the coating layer disposed on the inner peripheral surface of the first tube body is greater than the thickness of the coating layer disposed on the inner peripheral surface of the second tube body.

15. The medical instrument according to claim 14, wherein the part of the coating layer that coats the level difference portion is a convex protrusion that protrudes radially inward from the level difference portion.

16. The medical instrument according to claim 14, wherein the open distal end of the second tube body has a tapered outer surface which is inclined from a largest outer diameter on a proximal side to a smallest outer diameter on a distal side in the axial direction.

17. The medical instrument according to claim 16, wherein the coating layer is interposed between the inner peripheral surface of the first tube body and the tapered outer surface of the open distal end of the second tube body.

18. The medical instrument according to claim 14, wherein the coating layer is continuously formed on the inner peripheral surface of the first tube body and the inner peripheral surface of the distal end opening portion of the second tube body.

19. The medical instrument according to claim 14, wherein the biocompatible material is an antithrombotic material.

20. The medical instrument according to claim 19, wherein
the inner peripheral surface of the first tube body is made of a hydrophobic material and the inner peripheral surface of the second tube body is made of a hydrophobic material, the coating layer is not chemically bonded to the inner peripheral surfaces of the first and second tube bodies, and the coating layer has hydrophobicity and is formed of the antithrombotic material having a weight-average molecular weight of 400,000 or heavier.

* * * * *